(12) United States Patent
Courtney et al.

(10) Patent No.: US 8,435,225 B2
(45) Date of Patent: May 7, 2013

(54) EMBOLIZATION PROTECTION SYSTEM FOR VASCULAR PROCEDURES

(75) Inventors: Brian K. Courtney, Redwood City, CA (US); John M. MacMahon, Mountain View, CA (US); Thomas G. Goff, Mountain View, CA (US)

(73) Assignee: Fox Hollow Technologies, Inc., Redwood City, CA (US)

( * ) Notice: Subject to any disclaimer, the term of this patent is extended or adjusted under 35 U.S.C. 154(b) by 2308 days.

(21) Appl. No.: 10/903,523

(22) Filed: Jul. 30, 2004

(65) Prior Publication Data

US 2005/0004517 A1 Jan. 6, 2005

Related U.S. Application Data

(63) Continuation of application No. 09/872,068, filed on May 31, 2001, now Pat. No. 7,108,677.

(60) Provisional application No. 60/208,593, filed on Jun. 2, 2000.

(51) Int. Cl.
*A61M 31/00* (2006.01)
*A61M 29/00* (2006.01)
*A61F 11/00* (2006.01)

(52) U.S. Cl.
USPC .......... 604/509; 604/508; 604/510; 604/507; 604/96.01; 604/102.01; 606/108; 606/194

(58) Field of Classification Search ............... 604/96.01, 604/507–510, 101.01–101.05, 102.01, 102.02; 606/108, 191–192, 194, 200
See application file for complete search history.

(56) References Cited

U.S. PATENT DOCUMENTS

| | | | |
|---|---|---|---|
| 3,833,004 | A | 9/1974 | Vazquez et al. |
| 3,923,065 | A | 12/1975 | Nozick et al. |

(Continued)

FOREIGN PATENT DOCUMENTS

| | | |
|---|---|---|
| EP | 0 427 429 | 5/1991 |
| SU | 929111 | 5/1982 |

(Continued)

OTHER PUBLICATIONS

Ohki et al., "Efficacy of a Proximal Occlusion Catheter with Reversal of Flow in the Prevention of Embolic Events During Carotid Artery Stenting: An Experimental Analysis", Journal of Vascular Surgery (Mar. 2001) vol. 33, No. 3, p. 504-509.

(Continued)

*Primary Examiner* — Kevin C Sirmons
*Assistant Examiner* — Bradley G Thomas, Jr.
(74) *Attorney, Agent, or Firm* — Kilpatrick Townsend & Stockton LLP

(57) ABSTRACT

Apparatus and methods are described for effective removal of emboli or harmful fluids during therapeutic and diagnostic vascular procedures, such as angiography, balloon angioplasty, stent deployment, laser angioplasty, atherectomy, and intravascular ultrasonography. A catheter with an occluder mounted at its distal end creates an occlusion proximal to the lesion and provides a pathway for introducing a treatment catheter. Prior to, during or subsequent to the procedure, suction is activated to establish retrograde flow to remove emboli from the site. Additionally, a thin catheter with a distal fluid ejection nozzle may be introduced distal to the treatment site to rinse emboli from the treatment site. The suction flow and/or ejected fluid flow may be varied in a pulsatile manner to simulate regular blood flow and/or perturb settled emboli into being captured that may otherwise not be collected. The method establishes a protective environment before any devices enter the treatment site.

23 Claims, 15 Drawing Sheets

U.S. PATENT DOCUMENTS

| | | | |
|---|---|---|---|
| 4,024,873 A | 5/1977 | Antoshkiw et al. | |
| 4,148,319 A | 4/1979 | Kasper et al. | |
| 4,423,725 A | 1/1984 | Baran et al. | |
| 4,457,747 A | 7/1984 | Tu | |
| 4,655,746 A | 4/1987 | Daniels et al. | |
| 4,714,460 A | 12/1987 | Calderon | |
| 4,794,928 A | 1/1989 | Kletschka | |
| 4,832,028 A | 5/1989 | Patel | |
| 4,902,276 A | 2/1990 | Zakko | |
| 4,909,783 A | 3/1990 | Morrison | |
| 4,921,478 A | 5/1990 | Solano et al. | |
| 5,000,743 A | 3/1991 | Patel | |
| 5,030,227 A | 7/1991 | Rosenbluth et al. | |
| 5,071,407 A | 12/1991 | Termin et al. | |
| 5,092,839 A | 3/1992 | Kipperman | |
| 5,179,961 A | 1/1993 | Littleford et al. | |
| 5,188,592 A | 2/1993 | Hakki et al. | |
| 5,221,261 A | 6/1993 | Termin et al. | |
| 5,318,518 A | 6/1994 | Plechinger et al. | |
| 5,439,446 A | 8/1995 | Barry | |
| 5,462,529 A | 10/1995 | Simpson et al. | |
| 5,476,450 A | 12/1995 | Ruggio | |
| 5,496,267 A | 3/1996 | Drasler et al. | |
| 5,522,882 A | 6/1996 | Gaterud et al. | |
| 5,549,626 A | 8/1996 | Miller et al. | |
| 5,573,504 A | 11/1996 | Dorsey, III | |
| 5,601,591 A | 2/1997 | Edwards et al. | |
| 5,634,897 A | 6/1997 | Dance et al. | |
| 5,639,274 A | 6/1997 | Fischell et al. | |
| 5,653,689 A | 8/1997 | Buelna et al. | |
| 5,653,690 A | 8/1997 | Booth et al. | |
| 5,669,927 A | 9/1997 | Boebel et al. | |
| 5,749,890 A | 5/1998 | Shaknovich | |
| 5,827,229 A | 10/1998 | Auth et al. | |
| 5,833,644 A | 11/1998 | Zadno-Azizi et al. | |
| 5,833,650 A | 11/1998 | Imran | |
| 5,843,050 A | 12/1998 | Jones et al. | |
| 5,893,867 A | 4/1999 | Bagaoisan et al. | |
| 5,911,725 A | 6/1999 | Boury | |
| 5,938,645 A | 8/1999 | Gordon | |
| 5,968,017 A | 10/1999 | Lampropoulos et al. | |
| 5,971,990 A | 10/1999 | Venturelli | |
| 5,989,263 A | 11/1999 | Shmulewitz | |
| 5,997,562 A | 12/1999 | Zadno-Azizi et al. | |
| 6,007,545 A | 12/1999 | Venturelli | |
| 6,013,085 A | 1/2000 | Howard | |
| 6,019,772 A | 2/2000 | Shefaram et al. | |
| 6,022,336 A | 2/2000 | Zadno-Azizi et al. | |
| 6,050,972 A | 4/2000 | Zadno-Azizi et al. | |
| 6,068,608 A * | 5/2000 | Davis et al. | 604/4.01 |
| 6,068,623 A | 5/2000 | Zadno-Azizi et al. | |
| 6,135,991 A | 10/2000 | Muni et al. | |
| 6,146,370 A | 11/2000 | Barbut | |
| 6,152,909 A | 11/2000 | Bagaoisan et al. | |
| 6,156,005 A | 12/2000 | Theron | |
| 6,156,054 A | 12/2000 | Zadno-Azizi et al. | |
| 6,159,195 A | 12/2000 | Ha et al. | |
| 6,168,579 B1 * | 1/2001 | Tsugita | 604/96.01 |
| 6,190,332 B1 | 2/2001 | Muni et al. | |
| 6,206,868 B1 | 3/2001 | Parodi | |
| 6,214,026 B1 | 4/2001 | Lepak et al. | |
| 6,217,567 B1 | 4/2001 | Zadno-Azizi et al. | |
| 6,228,072 B1 | 5/2001 | Omaleki et al. | |
| 6,231,588 B1 | 5/2001 | Zadno-Azizi et al. | |
| 6,234,996 B1 | 5/2001 | Bagaoisan et al. | |
| 6,235,042 B1 | 5/2001 | Katzmann | |
| 6,254,563 B1 | 7/2001 | Macoviak et al. | |
| 6,258,061 B1 | 7/2001 | Drasler et al. | |
| 6,270,477 B1 | 8/2001 | Bagaoisan et al. | |
| 6,273,878 B1 | 8/2001 | Muni | |
| 6,287,271 B1 * | 9/2001 | Dubrul et al. | 604/22 |
| 6,290,689 B1 | 9/2001 | Delaney et al. | |
| 6,295,989 B1 | 10/2001 | Connors, III | |
| 6,312,407 B1 | 11/2001 | Zadno-Azizi et al. | |
| 6,319,229 B1 | 11/2001 | Kim et al. | |
| 6,325,777 B1 | 12/2001 | Zadno-Azizi et al. | |
| 6,325,778 B1 | 12/2001 | Zadno-Azizi et al. | |
| 6,338,709 B1 | 1/2002 | Geoffrion et al. | |
| 6,355,014 B1 | 3/2002 | Zadno-Azizi et al. | |
| 6,355,016 B1 | 3/2002 | Bagaoisan et al. | |
| 6,375,628 B1 | 4/2002 | Zadno-Azizi et al. | |
| 6,375,629 B1 | 4/2002 | Muni et al. | |
| 6,379,345 B1 | 4/2002 | Constantz | |
| 6,387,071 B1 | 5/2002 | Constantz | |
| 6,394,096 B1 | 5/2002 | Constantz | |
| 6,436,077 B1 | 8/2002 | Davey et al. | |
| 6,454,741 B1 | 9/2002 | Muni et al. | |
| 6,471,683 B2 | 10/2002 | Drasler et al. | |
| 6,485,500 B1 | 11/2002 | Kokish et al. | |
| 6,488,671 B1 | 12/2002 | Constantz et al. | |
| 6,527,979 B2 | 3/2003 | Constantz et al. | |
| 6,533,767 B2 | 3/2003 | Johansson et al. | |
| 6,562,020 B1 | 5/2003 | Constantz et al. | |
| 6,652,480 B1 | 11/2003 | Imran et al. | |
| 6,730,063 B2 * | 5/2004 | Delaney et al. | 604/173 |
| 6,849,068 B1 | 2/2005 | Bagaoisan et al. | |
| 7,141,045 B2 * | 11/2006 | Johansson et al. | 604/508 |
| 2001/0039411 A1 | 11/2001 | Johansson et al. | |
| 2001/0041865 A1 | 11/2001 | Delaney et al. | |
| 2002/0016564 A1 | 2/2002 | Courtney et al. | |
| 2002/0044907 A1 | 4/2002 | Constantz et al. | |
| 2002/0156430 A1 | 10/2002 | Haarala et al. | |
| 2002/0165574 A1 | 11/2002 | Ressemann et al. | |
| 2002/0165598 A1 | 11/2002 | Wahar et al. | |
| 2003/0018297 A1 | 1/2003 | Constantz | |
| 2003/0104073 A1 | 6/2003 | Johansson et al. | |
| 2004/0054347 A1 * | 3/2004 | Zadno-Azizi et al. | 604/509 |

FOREIGN PATENT DOCUMENTS

| | | |
|---|---|---|
| WO | WO 99/45835 | 9/1999 |
| WO | WO 00/76390 | 12/2000 |
| WO | WO 03/007797 A2 | 1/2003 |

OTHER PUBLICATIONS

Advanced Imaging Catheter [online], "Imaging Catheter Gives Surgeons the Inside Picture", [retrieved on Jul. 15, 2002]. Retrieved from the Internet: http://www.llnl.gov/str/daSilva.html, 5 pages total.

* cited by examiner

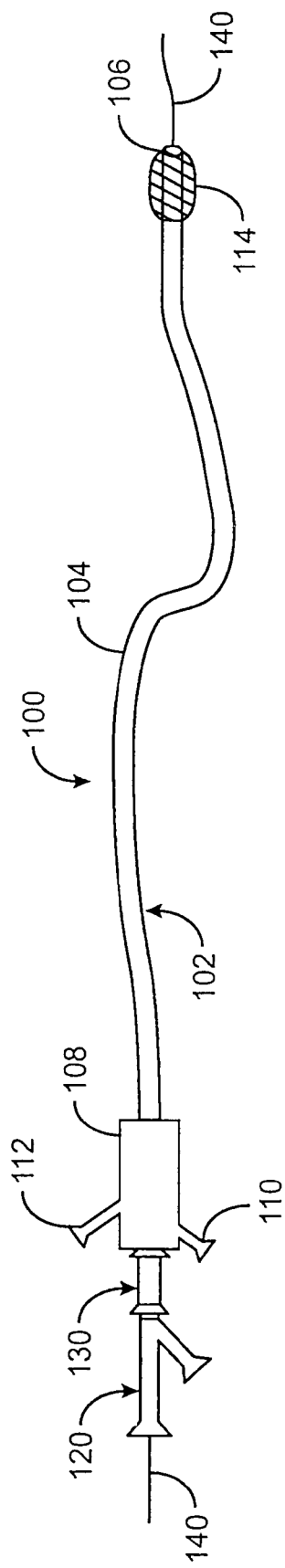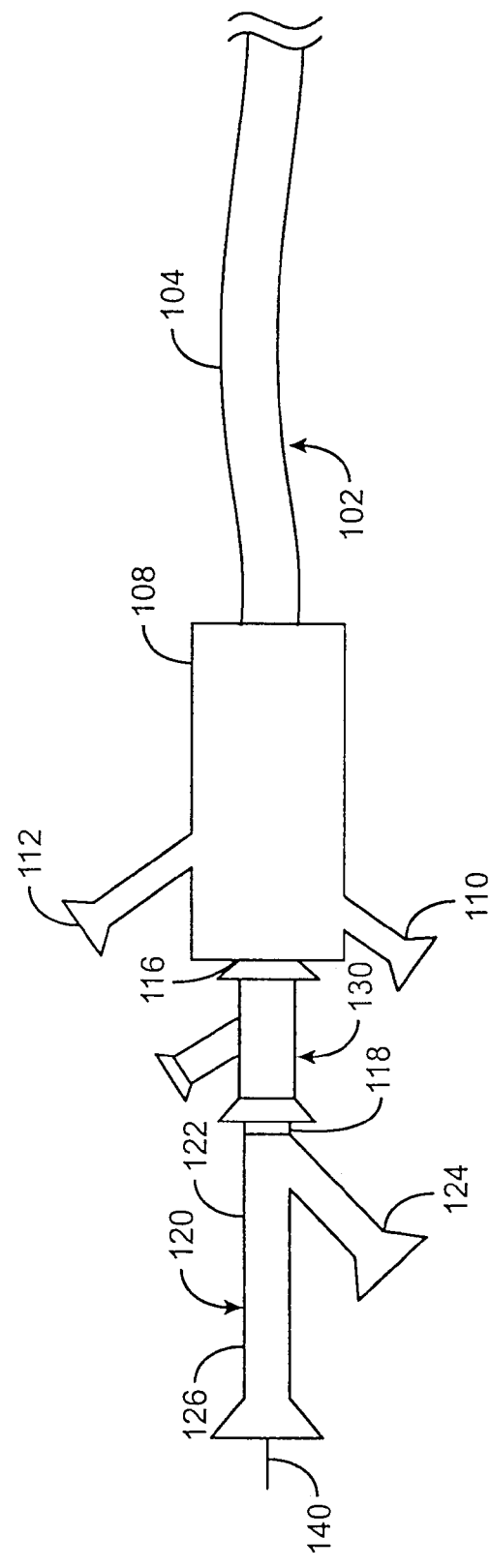
FIG. 1A
FIG. 1B

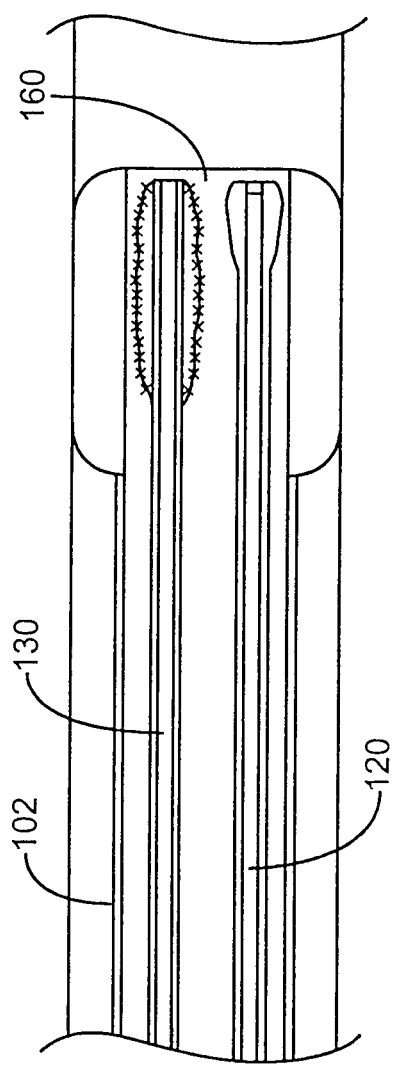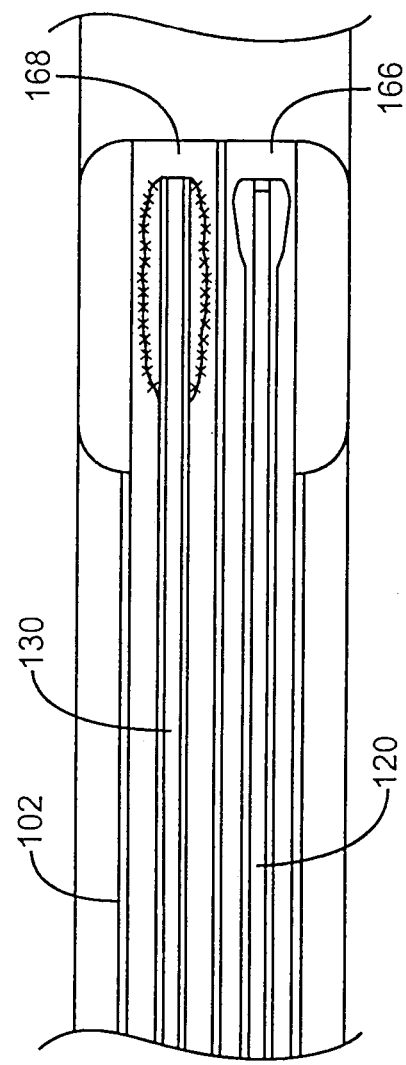
FIG. 3C
FIG. 3D

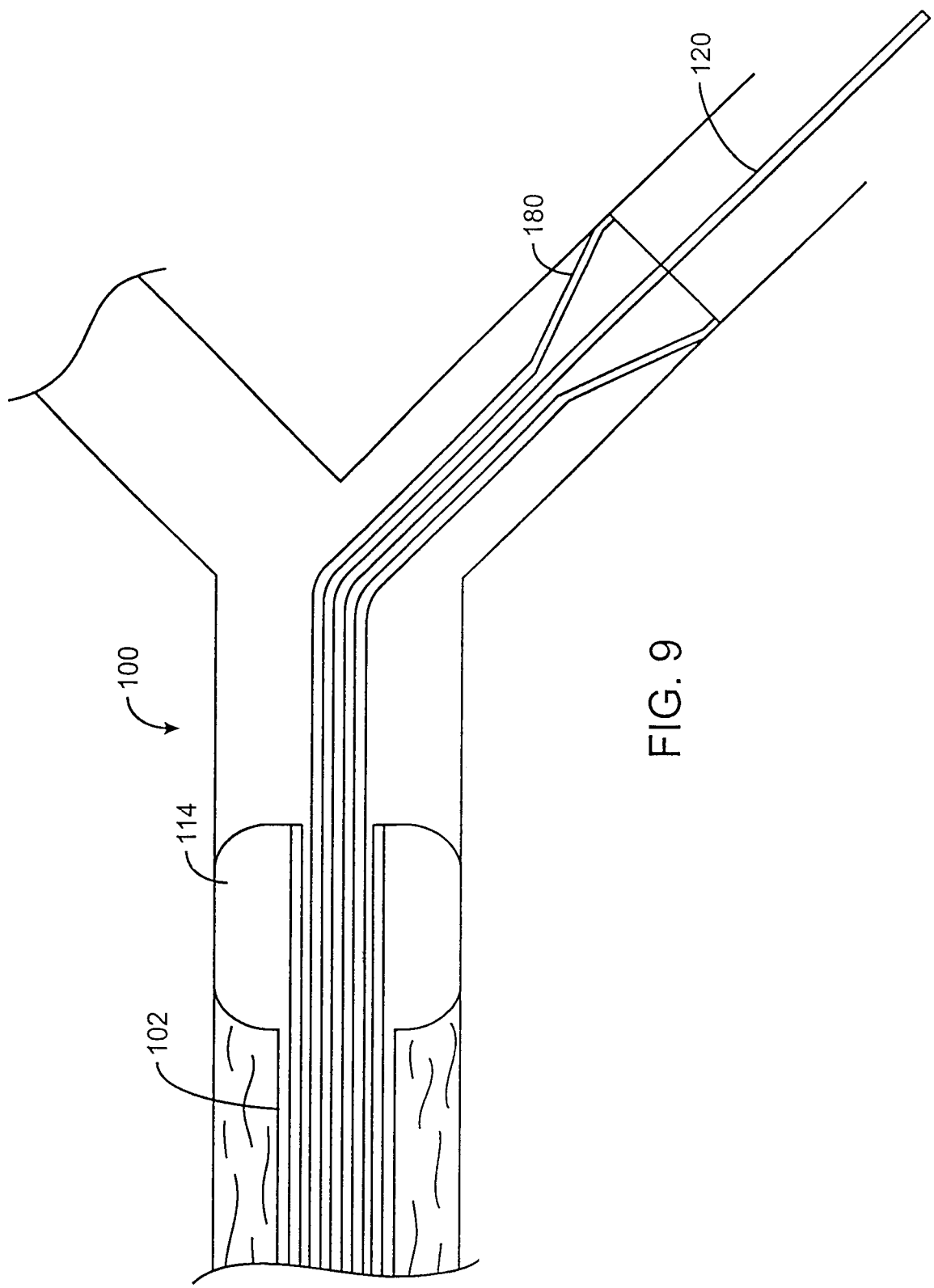

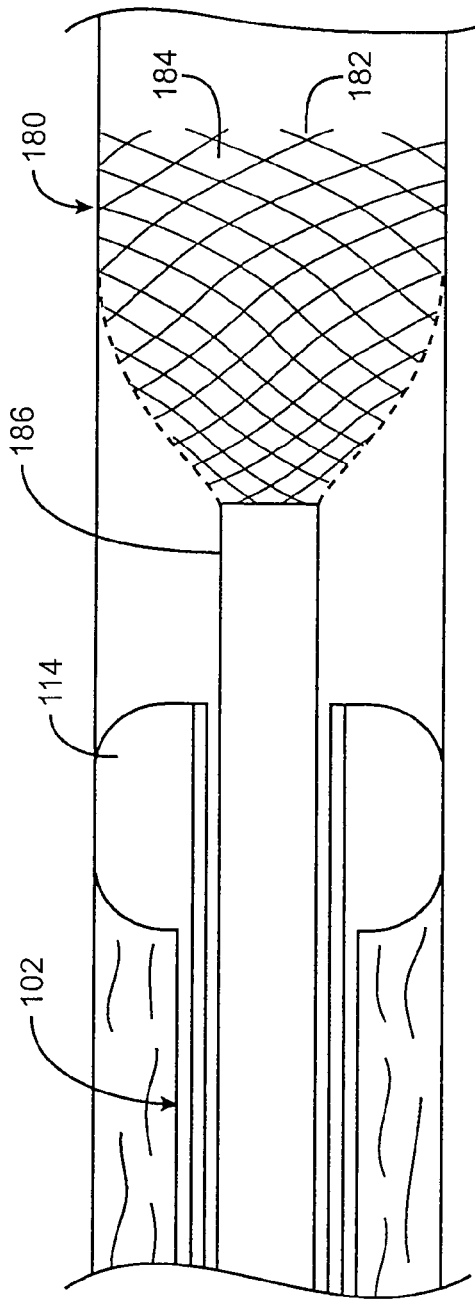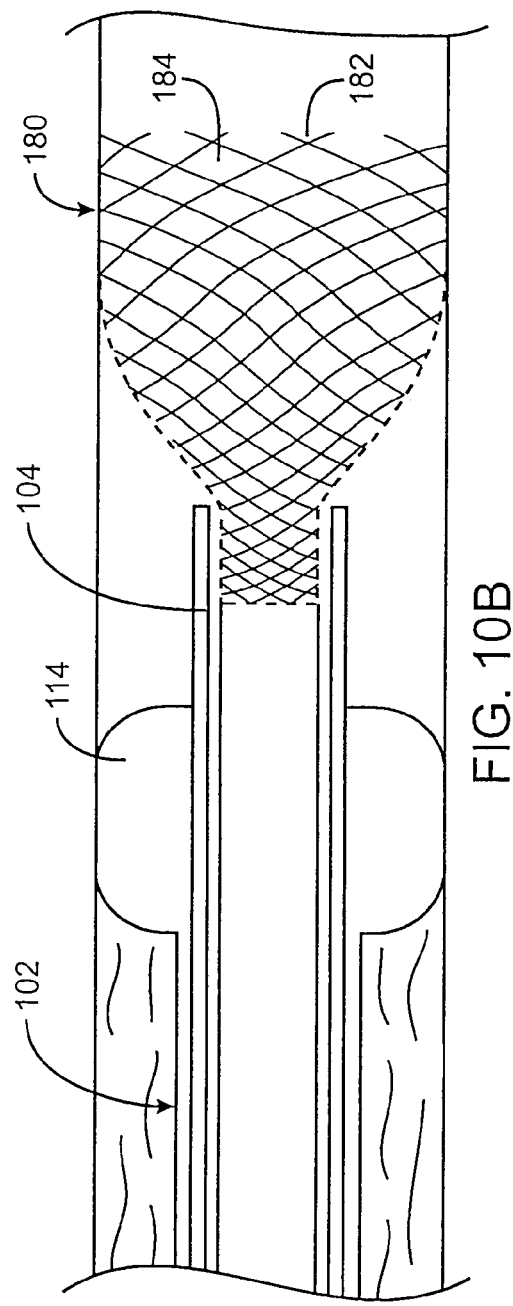

EMBOLIZATION PROTECTION SYSTEM FOR VASCULAR PROCEDURES

CROSS-REFERENCE TO OTHER APPLICATIONS

This application is a continuation of patent application Ser. No. 09/872,068 filed on May 31, 2001, now U.S. Pat. No. 7,108,677 which claims the benefit of U.S. Provisional Patent Application Ser. No. 60/208,593, filed Jun. 2, 2000. The priority of the prior applications are expressly claimed, and the disclosure of each of these prior applications is hereby incorporated by reference in its entirety.

FIELD OF THE INVENTION

This invention relates to the field of medical procedures on vessels of the circulatory system including catheter-based or other minimally invasive procedures. Sites within the vasculature at which the current invention may be employed include the carotid arteries, saphenous vein bypass grafts, and the renal arteries as well as other sites where harmful agents, such as emboli and radiopaque dyes, may be created or introduced during treatment and retrograde flow combined with a brief period of circulatory occlusion can be tolerated.

BACKGROUND OF THE INVENTION

The ability to effectively remove emboli and/or contrast agents during medical procedures in the circulatory system would have broad implications on how vascular disease and conditions are treated and complications are managed.

The use of procedures such as balloon angioplasty, laser angioplasty, chemical and mechanical methods of altering vessel walls, etc. pose a great risk to the patient as emboli may be released during such procedures. Once released, these emboli have a high likelihood of getting lodged into the vessels at a point of constriction downstream of their release point, causing the vessel to become occluded. Organs and tissues dependent on the occluded circulatory branch will have a depleted level of circulation and therefore suffer an increased likelihood of damage, including the possibility of organ failure and/or stroke.

Evidence exists that suggests that embolization is a serious complication. It can occur without a clinical triggering event, as in the case of a gradual increase in blood pressure, as well as during interventional procedures within the vasculature. Men in their sixth and seventh decades of life are most prone to cholesterol embolization, while the kidneys, spleen, pancreas, gastrointestinal tract, adrenals, liver, brain and testes are the organs most frequently reported as those affected. (Vidt D. G., Cholesterol emboli: a common cause of renal failure. *Annu Rev Med* 1997; 48:375-85.)

Common clinical procedures that might trigger an embolization event include stenting, fluoroscopy, angioplasty, and other operative as well as diagnostic procedures that occur in sites that communicate fluid within the vasculature. Furthermore, it is difficult to identify embolization as the source of any symptoms that are presented, because these symptoms can be similarly presented by several mechanisms other than embolization.

Other related problems may require the extraction of materials or fluids from the body to prevent embolization. For example, in the event of a patient being placed on a heart lung machine, the aorta will need to be clamped. Upon release of the clamp or equivalent, debris and/or emboli produced or accumulated as a result of the clamping may be in danger of proceeding throughout the body, including the cerebral vasculature. The current invention would be useful in removing these materials or fluids at or around the time at which the circulation in this region is restored to normal.

Yet another problem that often occurs during diagnostic and interventional procedures involves the introduction of potentially harmful fluids, such as radiopaque dyes used during fluoroscopy. Three common issues that may render a fluid harmful to the patient include high doses of the agent, immunological responses (i.e. allergic reactions) to the fluid (Back M. R., Angiography with carbon dioxide ($CO_2$) *Surg Clin North Am* 1998 August; 78(4):575-91) or heightened sensitivity of the patient to the fluid, as in the case of azotemic diabetics (Manske, C. L., Contrast Nephropathy in Azotemic Diabetic Patients Undergoing Coronary Angiography, *The American Journal of Medicine*, 1990 November, 89:615-620.) These may lead to organ failure or other complications. Renal failure due to the administration of contrast agent has been reported to be the third most common cause of in-hospital renal failure, surpassed only by hypotension and surgery. (Katzberg, R. W., Urography into the $21^{st}$ Century: New Contrast Media, Renal Handling, Imaging Characteristics, and Nephrotoxicity. *Radiology*, 1997 August, 204(2): 297-309.)

DESCRIPTION OF PRIOR ART

With respect to the prevention of problems created by the introduction of a fluid into the vasculature, such as radiopaque dyes, there is little in the way of prior art. Current techniques to minimize the associated problems include minimization of the amount of fluoroscopic dye introduced and the use of less toxic agents, such as $CO_2$. (Spinosa D. J., Renal insufficiency: usefulness of gadodiamide-enhanced renal angiography to supplement CO2-enhanced renal angiography for diagnosis and percutaneous treatment. *Radiology* 1999 March; 210(3):663-72.)

Regarding the prevention of embolization during vascular procedures, there are many described devices and methods to trap emboli. Many prior art devices involve the introduction of a filter distal to the site of a treatment. These devices rely on the flow of blood to force emboli into a filtering membrane, media or like structure. The Neuroshield by MedNova (UK) is an example of such a device. (Ohki, T, Roubin, G. S, et al, Efficacy of a filter device in the prevention of embolic events during carotid angioplasty and stenting: An ex vivo analysis, *Journal of Vascular Surgery*, December, 1999, 30(6):1034-44.)

Alternatively, the PercuSurge system (Zadno-Azizi, U.S. Pat. No. 6,022,336) establishes a complete occlusion to flow distal to the site of treatment and uses aspiration to attempt to remove embolic material. This patent and all other patents referred to herein are hereby incorporated by reference in their entirety.

Solano et al hold a patent (U.S. Pat. No. 4,921,478) for therapeutic interventions that describes means to occlude a vessel proximally to a treatment site. The occlusion consists of a funnel shaped balloon that is inflated proximal to the treatment site and which has a hole at the end of the funnel. Fluid and debris can be collected and effluxed through this hole towards the proximal end of the shaft and outside of the patient's body.

Finally, Parodi (U.S. Pat. No. 6,206,868) describes a protective device and method against embolization during treatment of carotid artery disease that applies active suction through the occlusion catheter to ensure regional reversal of blood flow within the blood vessel distal to the stenosis for capturing emboli during deployment of a stent. Such regional reversal of blood flow may be unnecessary and, in fact, may be contraindicated in patients at high risk for ischemic damage or with compromised collateral flow. A more localized reversal of blood flow in the vicinity of the stenosis provides ample embolic protection without the potential risks from inducing regional reversal of blood flow in the blood vessel distal to the stenosis.

SUMMARY OF THE INVENTION

The current invention describes tools and methods that enable the effective removal of emboli during a wide variety of vascular procedures, such as, but not limited to, angiography, balloon angioplasty, stent deployment, laser angioplasty, atherectomy, endarterectomy, intravascular ultrasonography and other similar therapeutic and diagnostic procedures. In general, a hollow catheter with a similarly hollow tip, creates an occlusion proximal to the lesion site. The inner lumen of the catheter communicates with the site of treatment which is distal to the occluder and provides a pathway through which the tools of the procedure, such as balloon catheters and stents, may be delivered. Either prior to, during or subsequent to the procedure, an active suction is activated to establish or contribute to retrograde flow through the site of the procedure, causing any emboli at the site of treatment to be simultaneously removed.

Additionally, a thin catheter with a distal fluid ejection nozzle may be introduced distal to the site of treatment at any time to provide a fluid source and/or to provide a method of rinsing the treatment site. Furthermore, the suction flow and/or ejected fluid flow may be made to vary in a pulsatile manner to simulate regular blood flow and/or to perturb settled emboli into being captured that may otherwise not be collected. The described method allows a protective environment to be established before any devices cross the site to be treated, which, compared to several other techniques for embolization protection, significantly reduces the likelihood of creating emboli before an effective capturing mechanism is established.

Furthermore, devices and methods to protect against complications caused by angiographic contrast agents are provided to enable better imaging when there is high sensitivity to such agents in susceptible people or susceptible locations, such as the renal arteries where complications are frequent.

BRIEF DESCRIPTION OF THE DRAWINGS

FIG. 1a is a perspective drawing of an embolization protection system constructed according to the present invention.

FIG. 1b is a detail drawing of a proximal portion of the catheter system of FIG. 1 showing the proximal adaptor.

FIG. 3c shows an alternate embodiment of the embolization protection system where the inner sheath and the treatment device are inserted parallel to one another through the outer catheter.

FIG. 3d shows an alternate embodiment of the embolization protection system where the inner sheath and the treatment device are inserted parallel to one another through dedicated lumens within the outer catheter.

FIG. 9 shows the use of the embodiment in FIG. 8 at a bifurcation in the vasculature.

FIGS. 10a and 10b depict an embodiment similar to that in FIG. 8 where the funnel shaped structure is specifically a lined self-expanding mesh funnel. 10a shows the lined self-expanding mesh funnel has its own delivery sheath, while 10b shows the lined self-expanding mesh funnel using the outer sheath as the delivery sheath.

DETAILED DESCRIPTION OF THE INVENTION

Figure 11:
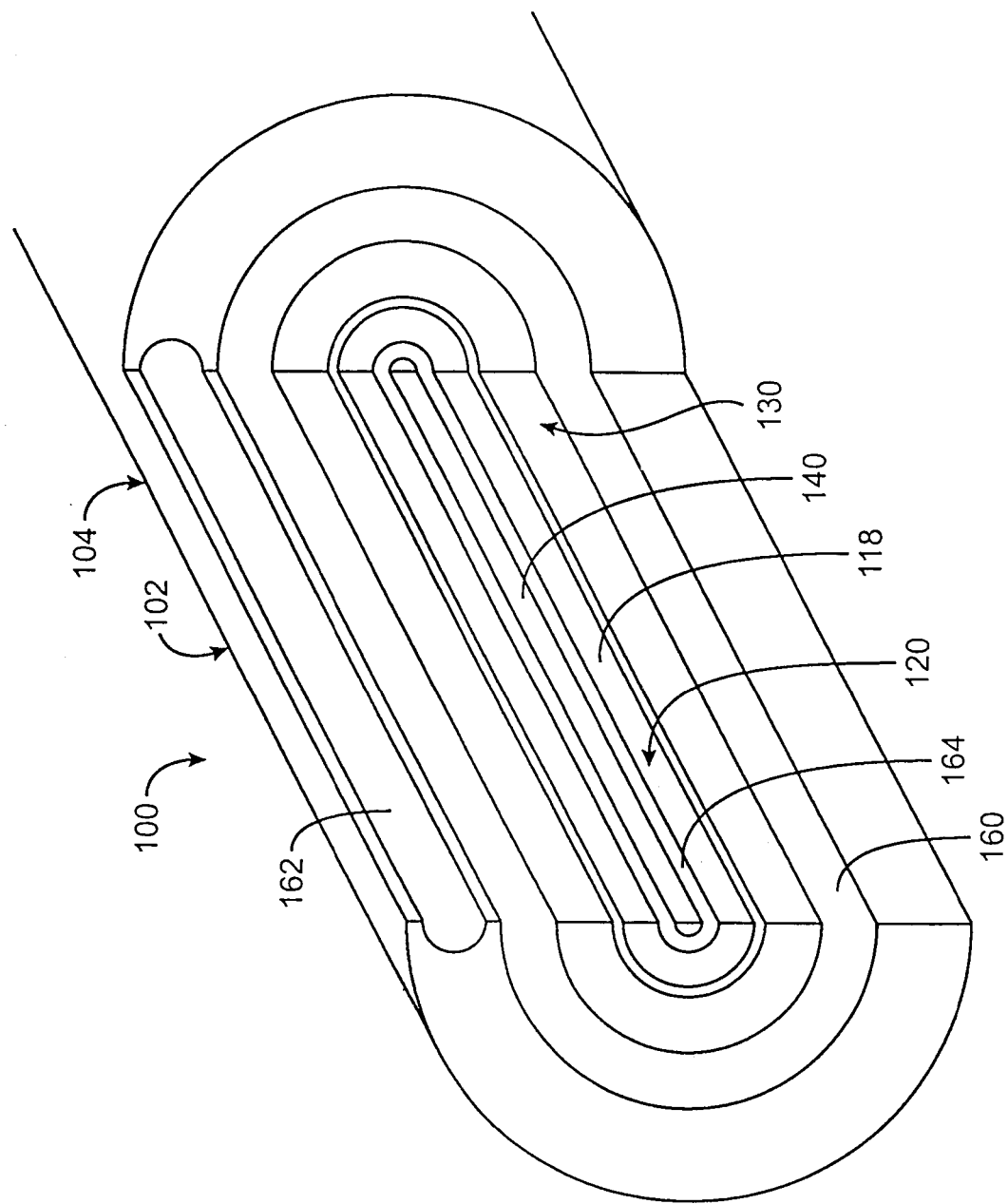
FIG. 11 is a cutaway view showing the coaxial arrangement of the catheter shafts in the distal embolic protection system.

FIG. 1a is a perspective drawing of an embolization protection system 100 constructed according to the present invention. FIG. 1a shows an outer catheter 102 having an extended shaft 104 with a distal end 106 and a proximal adaptor 108. FIG. 1b is a detail drawing of a proximal portion of the catheter system of FIG. 1 showing the proximal adaptor 108. FIG. 11 is a cutaway view showing the coaxial arrangement of the catheter shafts in the distal embolic protection system. The proximal adaptor 108 may be an injection molded part or it may be assembled from separate components. The proximal adaptor 108 has several ports: one is an efflux port 110 where fluid is removed from the suction or efflux lumen 160 of the catheter 102, an optional inflation port 112 in connection with an inflation lumen 162 for inflating an occluding balloon 114 at or near the distal end 104, for those embodiments with either a balloon or self-expanding foam as the occluding mechanism, a treatment port 116 in connection with the efflux lumen 160, through which an inner sheath or catheter 120 is insertable and through which treatment devices 130 such as angioplasty balloons, stents, etc. can optionally be delivered coaxially around the inner catheter 120. Preferably, the treatment port 116 will include a hemostasis valve or a compression fitting for sealing around the inner sheath 120 and treatment device 130.

The efflux port 110 of the outer catheter 102 may be connected to a suction pump for active aspiration or it may be connected to a gravity drain or siphon drain. The flow rate through the suction or efflux lumen 160 can be regulated by adjusting the pumping rate and/or with a stopcock or other valve connected to the efflux port 110. Alternatively, flow rate through the suction or efflux lumen 160 can be regulated by either raising or lowering the siphon sink or gravity drainage reservoir.

The inner sheath 120 has a proximal fitting 122 having an influx port 124 connected to the rinse or irrigation lumen 164 within the shaft 118 of the inner sheath 120 through which fluid is injected for infusion or irrigation through a nozzle 150 in the distal tip 128. (shown in FIG. 3) of the inner sheath 120 and a guidewire port 126 for insertion of a guidewire 140. The guidewire port 126 may be connected to the irrigation lumen 164 for coaxial insertion of the guidewire 140 through the irrigation lumen 164. Alternatively, a dedicated guidewire lumen may be provided within the shaft 118 of the inner sheath 120 Preferably, the guidewire port 126 will include a hemostasis valve or a compression fitting for sealing around the guidewire 140. The influx port 124 can be connected to a pump or a syringe as a source of irrigation or rinsing fluid.

Figure 2:
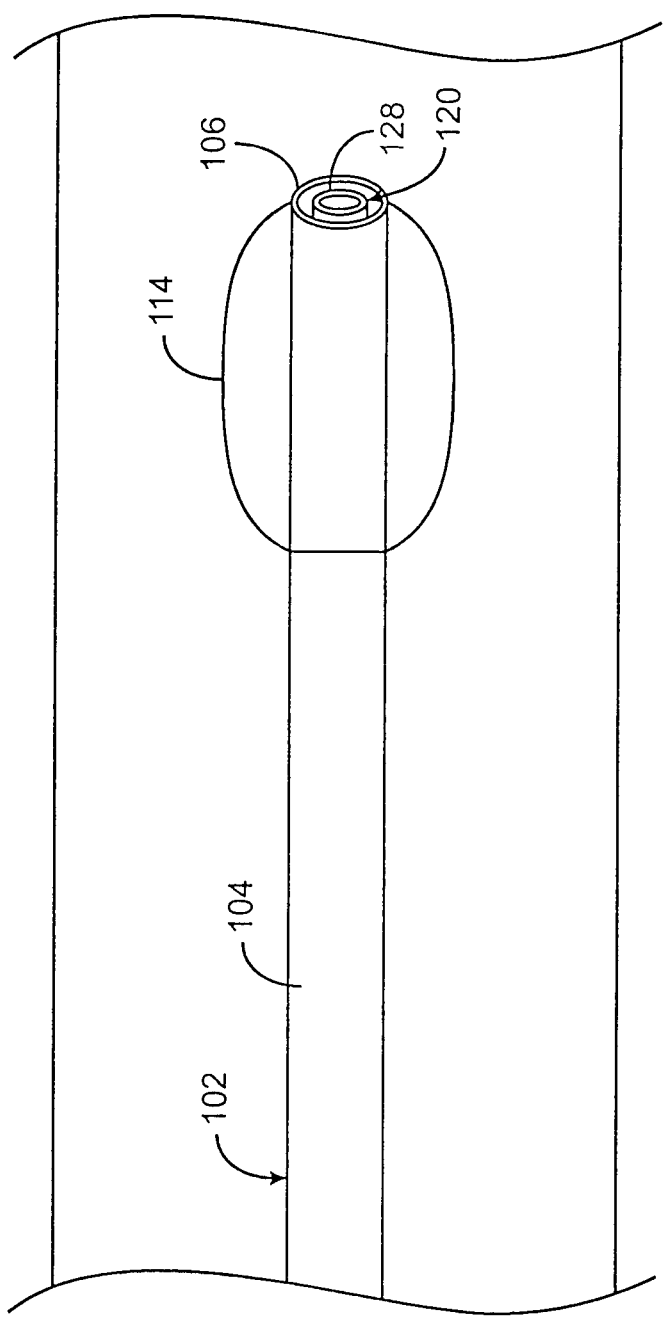
FIG. 2 is a perspective drawing of the tip in the deflated configuration within a vessel.
Figure 3A:
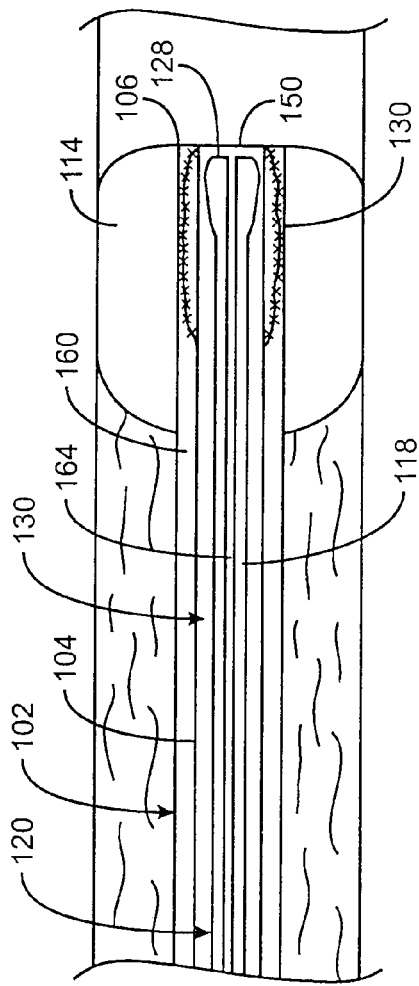
FIG. 3a is a longitudinal cross-sectional drawing of the tip in the inflated configuration within a vessel. The fluid delivery nozzle is retracted inside the tip of the occlusion sheath.
Figure 3B:
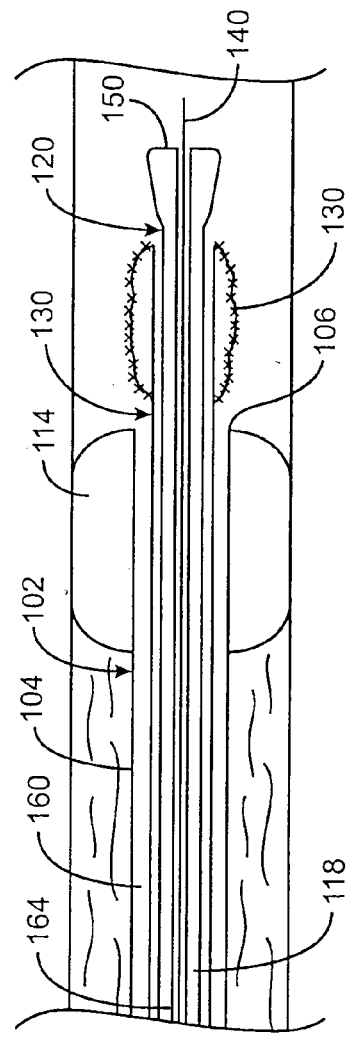
FIG. 3b is similar to that in FIG. 3a with the fluid delivery nozzle extended out from the occlusion sheath.

FIGS. 2, 3a and 3b show the distal tip 106 of the outer catheter 102. FIG. 2 is a perspective drawing of the distal tip 106 of the outer catheter 102 with the occluder 114 in the deflated configuration within a vessel. The distal tip 128 of the inner sheath 120 is visible within the outer catheter 102. FIG. 3a is a longitudinal cross-sectional drawing of the distal tip 106 of the outer catheter 102 with the occluder 114 in the inflated configuration within a vessel. The fluid delivery nozzle 150 of the inner sheath 120 is retracted inside the tip 106 of the outer catheter 102. FIG. 3b is similar to that in FIG. 3a with the fluid delivery nozzle 150 extended out from the outer catheter 102. The occlusion balloon 114 is in fluid communication with a separate inflation lumen 162 in the extended shaft 104 (as shown in FIG. 11), which in turn is in fluid communication with the inflation port 112 as described above. An auxiliary treatment means 130 (e.g. a stent or angioplasty balloon or some other device) is positioned coaxially around the inner sheath 120. The distal tip 128 of the inner sheath 120 comprises a rinse nozzle 150, which supplies a rinsing fluid to the vessel distal to the induced occlusion.

In the application where emboli produced by a treatment are to be collected by aspiration; the outer catheter 102 is delivered such that the uninflated occlusion balloon 114 is position just proximally to the treatment site. The occlusion balloon 114 is then inflated and the inner sheath 120 is extended distally past the treatment site. The treatment device 130 is then activated. Simultaneously, there may be aspiration occurring through the suction lumen 160 and/or rinsing fluid being ejected through the rinse nozzle 150.

Aspiration and the ejection of rinsing fluid will cause a flow of fluids proximally through the suction lumen 160 and out the suction port 110 at the proximal end of the outer catheter 102, taking debris with it.

FIG. 3c shows an alternate embodiment of the embolization protection system wherein the inner sheath 120 and the treatment device 130 are inserted parallel to one another through the outer catheter 102 rather than in a coaxial relationship. This parallel arrangement allows the inner sheath 120 and the treatment device 130 to be advanced and retracted or exchanged independently of one another. The inner sheath 120 and the treatment device 130 may both pass through the suction lumen 160 of the outer catheter 102. Alternatively, one or both of the inner sheath 120 and the treatment device 130 may be inserted through a dedicated lumen 166, 168 within the shaft 104 of the outer catheter 104, as shown in FIG. 3d.

The dimensions of the embolization protection system 100 may be varied to adapt the system to various applications within the body. The shaft 104 of the outer catheter 102 is preferably constructed with an outside diameter of approximately 3-12 F (approximately 1-4 mm diameter) with a suction lumen 160 sized to accept a treatment device 130 with a shaft size of approximately 1-4 F. The shaft 104 may be of a constant diameter or it may taper down toward the distal end 106 to reduce resistance to blood flow at the treatment site. The shaft 104 may be constructed from an extruded polymer, such as, but not limited to, polyethylene, polyurethane, nylons, e.g. PEBAX, with a lubricious inner coating, such as TEFLON, and may be reinforced with braided or coiled wires or fibers. The inflation lumen 162 may be embedded within the wall of the shaft 104 or it may be constructed of a separate piece of tubing that extends parallel to the shaft 104.

The dimensions of the embolization protection system 100 may also be varied to adapt the system for introduction via various access sites in the vasculature. For treatment of the carotid arteries with introduction via a femoral artery access site, the length of the outer catheter 102 is preferably in the range of approximately 140-150 cm and the lengths of the treatment device 130 and the inner sheath 120 are preferably in the range of approximately 160-180 cm. The diameter and length dimensions may be adjusted as appropriate for applications at other treatment sites and/or for other access sites, such as the brachial artery, subclavian artery, etc. In addition, these dimensions may also be adjusted as appropriate for applications in pediatric or veterinary patients.

The occluder 114 will preferably have a deflated diameter as small as possible for easy passage through the arteries and an expanded diameter sufficient to occlude blood flow in the artery proximal to the treatment site. For use in the carotid arteries, the occluder 114 will preferably have an expanded diameter of approximately 8-9 mm. For use in the coronary arteries, the occluder 114 will preferably have an expanded diameter of approximately 3-6 mm. For use in the aorta, the occluder 114 will preferably have an expanded diameter of approximately 20-50 mm. The occluder 114 may be constructed as an inflatable balloon made from an elastic material, such as, but not limited to, silicone, polyurethane, polyisoprene, latex, rubber.

Alternatively, the occluder 114 may be constructed as a self-expanding occluder, as a self-expanding foam funnel, or as funnel-shaped balloon 170 with connections between walls, as described below in connection with FIG. 4. A self-expanding occluder may be made of open-cell foam surrounded by an airtight outer envelope, such as silicone, which is delivered in a compressed state. In order to deploy the occluding mechanism, air or a fluid is allowed to enter the open-cell foam via an inflation lumen. To contract the occluding mechanism, air or fluid is actively pumped out of the open-cell foam, via the inflation lumen.

The shaft 118 of the inner sheath 120 is preferably constructed with an outside diameter of approximately 1-10 F (approximately 0.3-3.3 mm diameter) with an irrigation lumen 164 sized to accept a guidewire, such as an 0.010, 0.014 or 0.018 inch diameter steerable guidewire or a standard construction or steerable 0.032, 0.035 or 0.038 inch diameter guidewire. If the system 100 is used with an optional treatment device 130, the shaft 118 of inner sheath 120 is preferably constructed with an outside diameter of approximately 1-3 F to accommodate a 3-4 F treatment device 130 coaxially over the inner shaft 118. The shaft 118 is preferably made with a thin-wall construction with good column strength for pushability. Suitable materials for the shaft 118 include, but are not limited to, polyimide tubing, braid reinforced polyimide tubing, stainless steel hypotube and superelastic NiTi alloy tubing. Optionally, the shaft 118 may have a lubricious inner coating, such as TEFLON.

Figure 4:
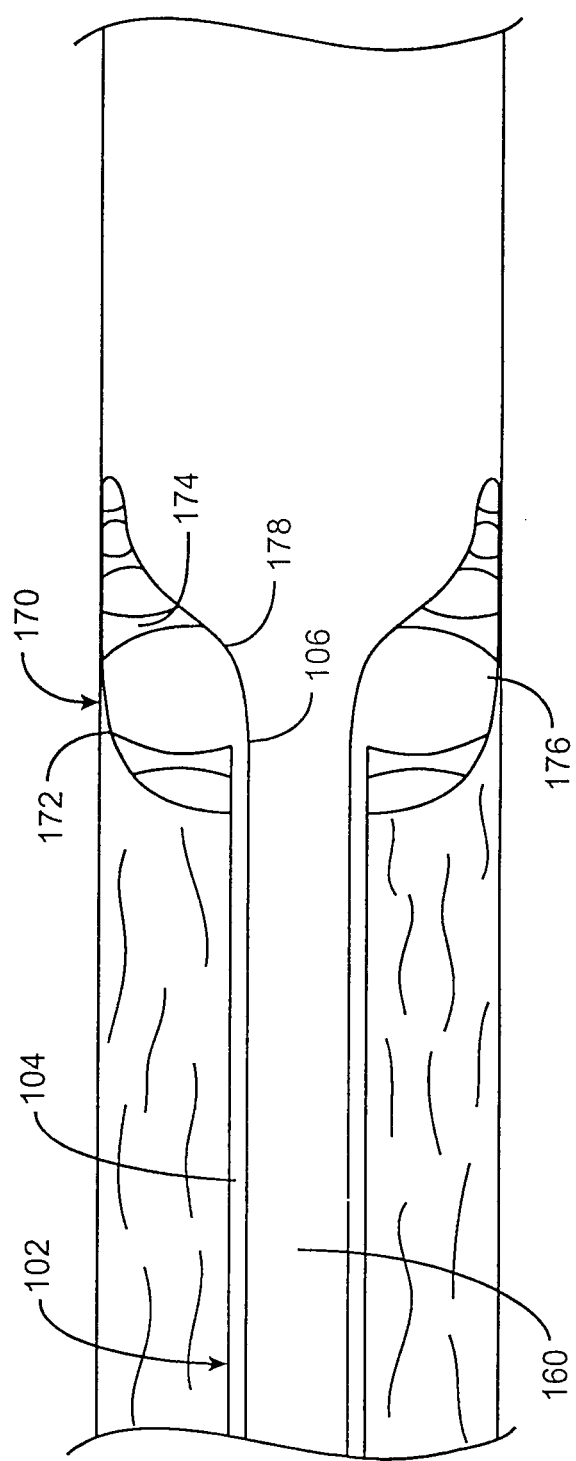
FIG. 4 is a longitudinal cross-sectional drawing of the tip that has connections between the walls of the inflated occlusion balloon to produce a desired shape in the inflated state.

FIG. 4 shows a funnel-shaped occlusion balloon 170 mounted at the distal end 106 of the shaft 104 of the outer catheter 102. The funnel-shaped occlusion balloon 170 may be used in place of the occlusion balloon 114 shown in FIG. 1 or it may be used in addition to the occlusion balloon 114, as shown below in FIG. 8. The outer shell 172 of the balloon 170 is formed using a mold of the desired shape. There are cross members 174 that link the inner 178 and outer 172 walls of the balloon 170 together, extending from one wall to the other through the inflation chamber 176. These cross members 174 enable the balloon 170 to take the desired form when inflated. These cross members 174 can be added to the balloon 170 during manufacturing either by accounting for them in the original mold or by adding them after the molding process of the walls using any combination of techniques that would include the use of adhesives, thermal bonding and other commonly used methods for joining polymeric surfaces together.

Figure 5A:
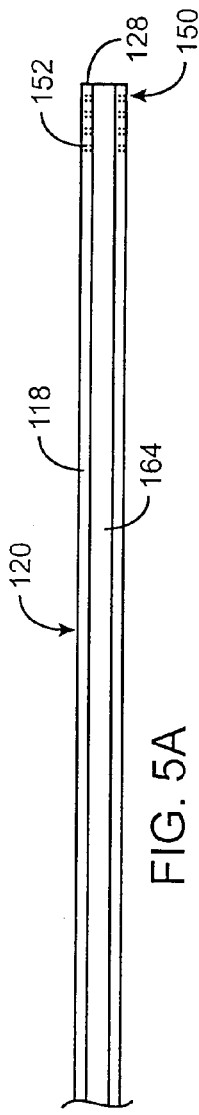
FIGS. 5a-5d show different configurations for the rinse nozzle at the distal end of the inner sheath.
Figure 5B:
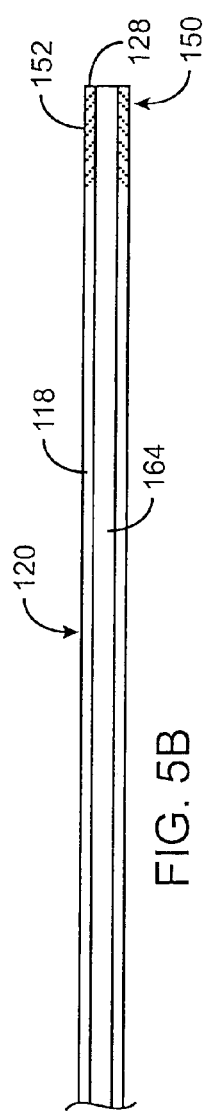
Figure 5C:
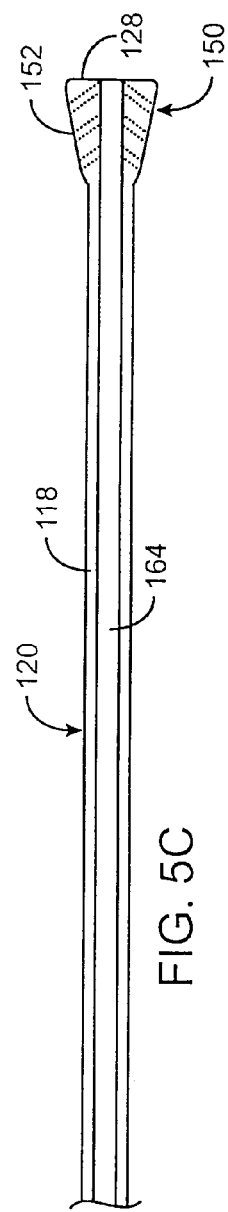
Figure 5D:
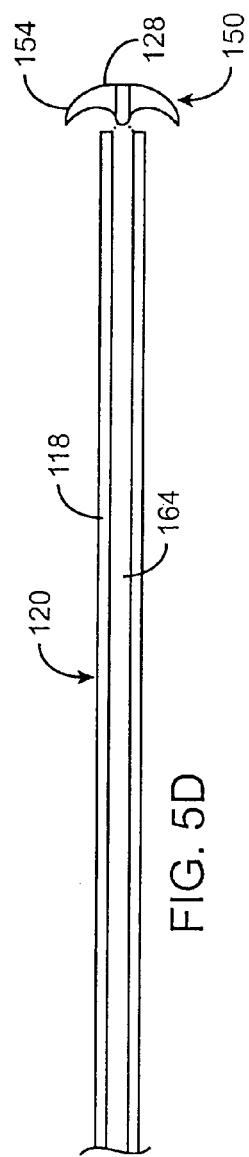

FIGS. 5*a*-5*d* show many different configurations for the rinse nozzle 150 at the distal end 128 of the shaft 118 of the inner sheath 120. FIG. 5*a* shows a rinse nozzle 150 with perforations 152 that are generally perpendicular to the longitudinal axis of the sheath 120. FIG. 5*b* and 5*c* show rinse nozzles 150 with perforations 152 that are angled such that the fluid is ejected with a component of its flow in the proximal direction to assist in producing the desired flow pattern. FIG. 5*d* shows another configuration with an umbrella-shaped flow diverter 154 that is integrated with the distal wall 118 of the inner sheath 120.

Either or both of the rinsing and aspiration actions can be controlled such that they occur in pulsatile and/or directionally varying manners. The goal of such a variation in flow within the vessel lumen adjacent to the treatment site is to better dislodge any particles that may get stuck along the surfaces of the vessel under what would otherwise be a strictly unidirectional constant flow. If the intensity of flow is similar to that encountered within the treated vessel segment under normal conditions, such as those experienced prior to or following an intervention, then there is a higher likelihood that any debris which would dislodge following an intervention would be captured during the intervention. Such physiologically relevant levels of flow during the capture of debris may therefore have a higher likelihood of improving a patient's outcome.

Physiologically relevant and pulsatile flows are advantageous in that they treat the vessels as flexible dynamic structures. The physiologically relevant flow and pulsatile nature of the rinsing or irrigation allows the vessel walls to expand and contract in their natural response to such conditions. From an embolic protection standpoint, this will help to release emboli from the vessel walls that may not be readily extracted using nonphysiological and/or nonpulsatile flows. For therapeutic treatment, this will help the circulation to communicate a delivered agent to the vessel walls and/or its associated covering. In the imaging case, a region containing a rigid calcified plaque or an aneurysm may be more clearly delineated with physiologically relevant and/or pulsatile flows. Physiological flow rates in a vessel are meant to include normal blood flow rates and/or normal blood velocities in the same vessel at rest and up to full exertion.

Figure 6:
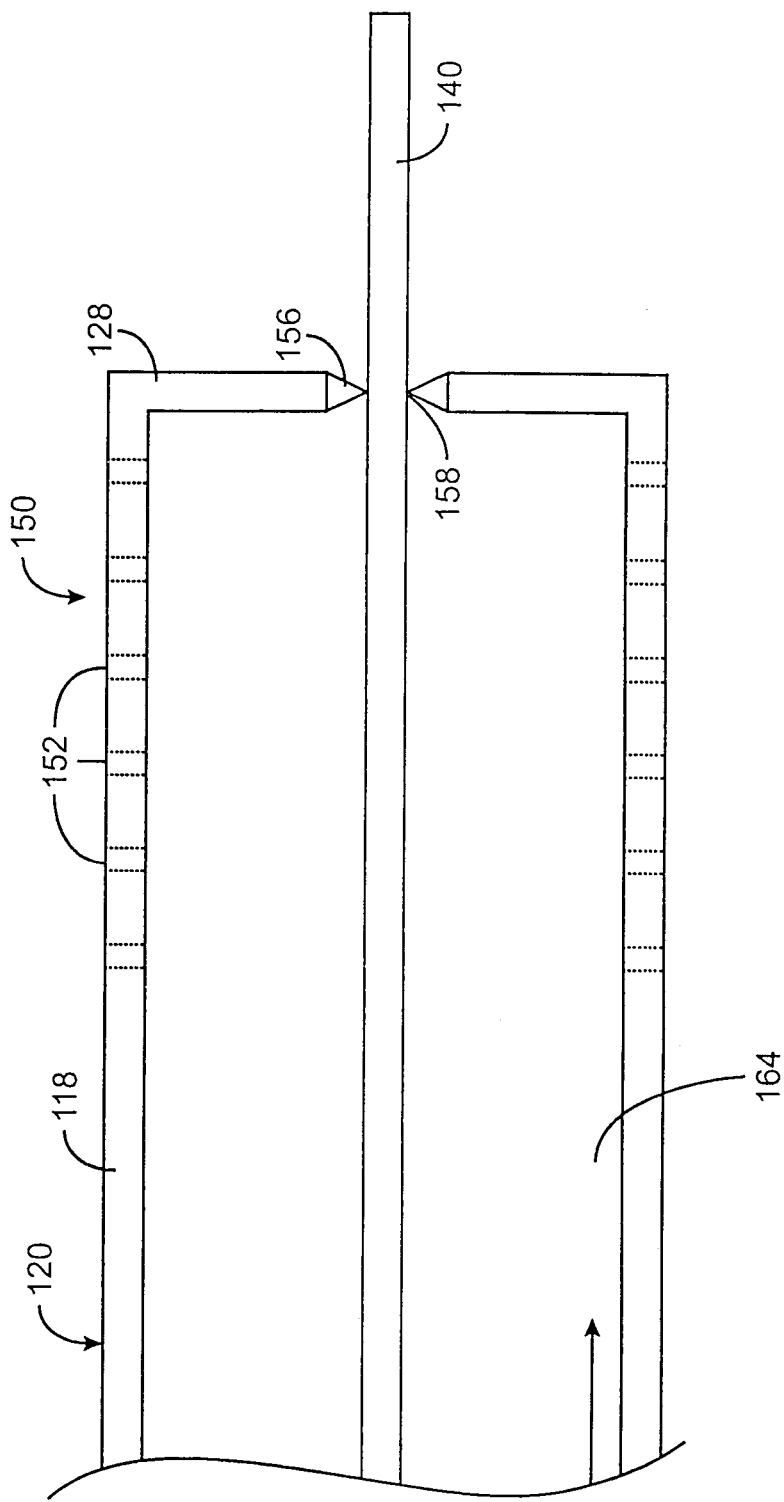
FIG. 6 is a longitudinal cross-sectional drawing of the irrigation tip where the guidewire passes through the irrigation lumen and exits the irrigation lumen through a semi-compliant stopper.

FIG. 6 shows a configuration of the distal end 128 of the inner sheath 120 which accommodates a guidewire 140 through the irrigation lumen 164. The guidewire 140 exits the irrigation lumen 164 distally through a seal 156 made of a semi-compliant material, such as rubber or the like, that creates a seal such that the rinse fluid does not substantially escape through the end hole 158 through which the guidewire 140 passes outside of the inner sheath 120.

Figure 7:
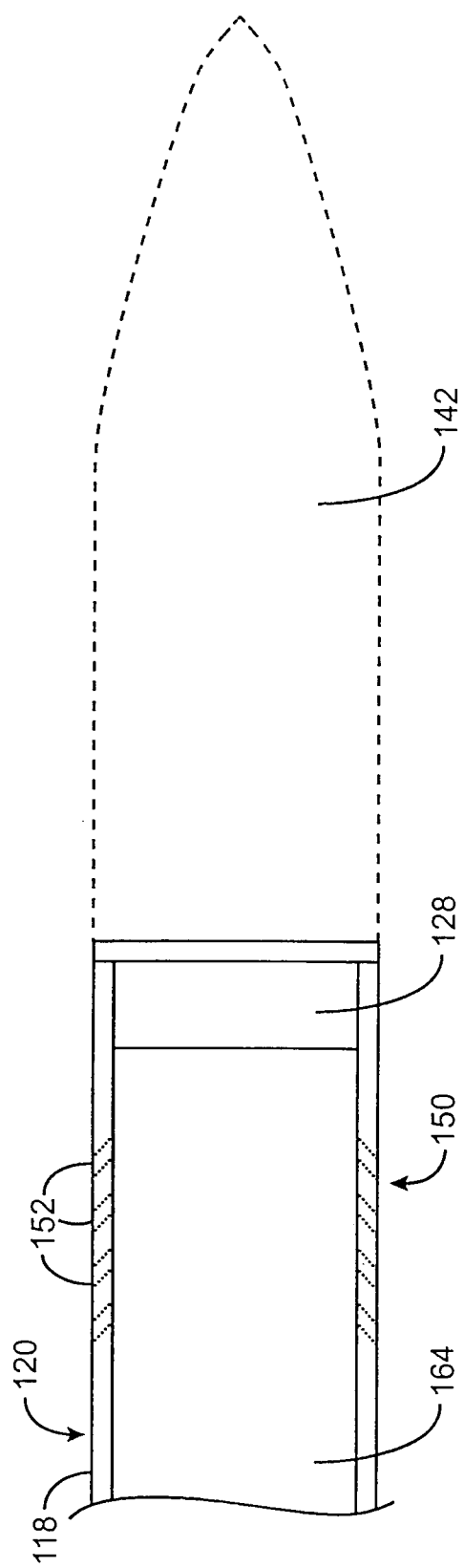
FIG. 7 is a longitudinal cross-sectional drawing of the irrigation tip without a channel for a separate guidewire.

FIG. 7 shows a configuration of the inner sheath 120 which does not accommodate a guidewire and has a closed distal end 128. Optionally, this configuration of the inner sheath 120 may have an added guidewire tip 142 fixedly attached to the distal end 128 of the shaft 118 distal to the rinse nozzle 150.

Figure 8:
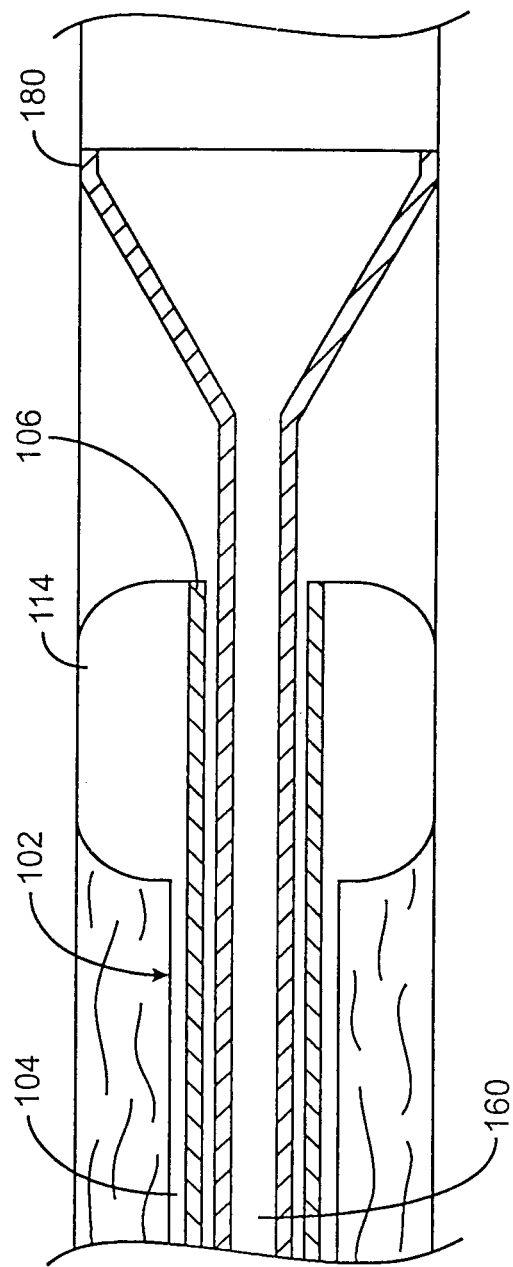
FIG. 8 depicts an alternative form of the device wherein the occlusion mechanism is in the form of a balloon, but an independent component is used to produce a funnel shape and direct the flow of debris into the suction lumen.

FIG. 8 shows a configuration of the distal end 106 of the extended shaft 104 of the outer catheter 102 where there is a balloon 114 to create the occlusion of flow and a separate funnel-shaped structure 180, which directs debris into the suction lumen 160. The inner sheath 120 has been omitted from this view for clarity of illustration. In one embodiment, the funnel-shaped structure 180 may take the form of a funnel-shaped balloon 170, as shown in FIG. 4. Alternatively, the funnel-shaped structure 180 may be in the form of a lined self-expanding mesh funnel, a self-expanding polymeric funnel or some other form, as shown here in FIG. 8. As shown in FIGS. 10*a* and 10*b*, the lined self-expanding mesh funnel 180 may be constructed with braided strands 182 of a highly elastic material, such as spring-tempered stainless steel or a superelastic or shape-memory NiTi alloy, with an impermeable liner 184, such as a polymer film or coating, or with a fine mesh liner, such as woven DACRON, GORTEX, to capture emboli and direct them into the efflux or suction lumen 160. The funnel-shaped structure 180 will preferably have a collapsed diameter as small as possible for easy passage through the arteries and an expanded diameter sufficient to occlude blood flow in the artery proximal to the treatment site. For use in the carotid arteries, the funnel-shaped structure 180 will preferably have an expanded diameter of approximately 8-9 mm.

Alternatively, the funnel-shaped structure 180 could be made of self-expanding material, with a construction similar to the self-expanding occluder described above. If the self-expanding material were to be open-cell foam, another inflation lumen is added to the device to allow inflation and deflation of the self-expanding foam funnel-shaped structure 180.

FIG. 9 shows the embodiment of embolization protection system 100 of FIG. 8 in use at a point of bifurcation, where the treatment site is in one of the forks of the vessel and the occlusion site is proximal to the bifurcation. Such a configuration makes it easier to treat sites of disease in the vicinity of a bifurcation, which suffer from a heightened frequency of pathological lesions relative to other regions of the circulatory system.

Another method for treatment at the point of a bifurcation in a vessel is to place the embolization protection system 100 in one branch of the vessel and to place a second occluder in the other branch of the vessel to prevent collateral backfilling of the vessel being treated or for added protection from potential emboli being washed downstream by blood flow through the other branch. The second occluder may be a second embolization protection system 100 or it may be a simple occlusion balloon catheter. For example, the embolization protection system 100 may be placed with the occluder 114 proximal to a lesion site in the internal carotid artery and an occlusion balloon catheter may be deployed to occlude the collateral external carotid artery. Cross flow between branches in a bifurcated vessel can also be managed by regulating the flow rate through the efflux lumen 160 of the outer catheter 102.

When the funnel-shaped structure 180 is in the form of a lined self-expanding mesh funnel, the system also preferably includes a delivery sheath that serves the purpose of holding the lined self-expanding mesh funnel in a long and thin conformation. However, the natural tendency of the lined self-expanding mesh funnel is to be in a shorter and radially extended conformation. When an operator partially extends a lined self-expanding mesh funnel out of the delivery sheath the lined self-expanding mesh funnel assumes a funnel shape. FIGS. 10a and b show two different forms of the delivery sheath. In FIG. 10b, the shaft 104 of the outer catheter 102 (i.e. the wall of the suction lumen 160) serves the purpose of acting as the delivery sheath for the funnel-shaped structure 180. This means that the funnel-shaped structure 180 is deployed at a preset and minimal distance distal from the occlusion site. Alternatively, as shown in FIG. 10b, a separate delivery sheath 186 may be provided for the funnel-shaped structure 180 so that it can travel longitudinally and independently of the outer catheter 102 and the inner sheath 120 (shown in FIG. 9) to deliver the funnel-shaped structure 180. This makes it possible to selectively place the funnel-shaped structure 180 at any of several longitudinal positions distal to the occlusion site.

Another use of the embolization protection system 100 can be in treating any region that may have reason for extraction of material or fluids. For example, in the event of a patient being placed on a heart-lung machine, the aorta will need to be clamped. Upon release of the clamp or equivalent, debris and/or emboli may be in danger of proceeding throughout the body and to the brain. This embolization protection system 100 can be introduced after the clamp is released and prior to initiation of normal flow from the beating heart.

This combined introduction of a physiologically relevant flow, perhaps again of a pulsatile nature, will allow for removal of this debris, such as emboli, prior to full blood flow and aid in the removal of any loose debris/emboli that may soon depart and become problematic to the patient once exposed to the normally pulsatile flow of the heart.

The flow rates supplied will be of such a nature that the tissue/vessels of interest will be exposed to physiologically relevant flow rates while the debris released or collected by that flow is collected in a controlled fashion. This would substantially benefit the outcome of the procedure by diminishing the presence of debris, such as emboli, in the cardiovascular system.

Figure 12:
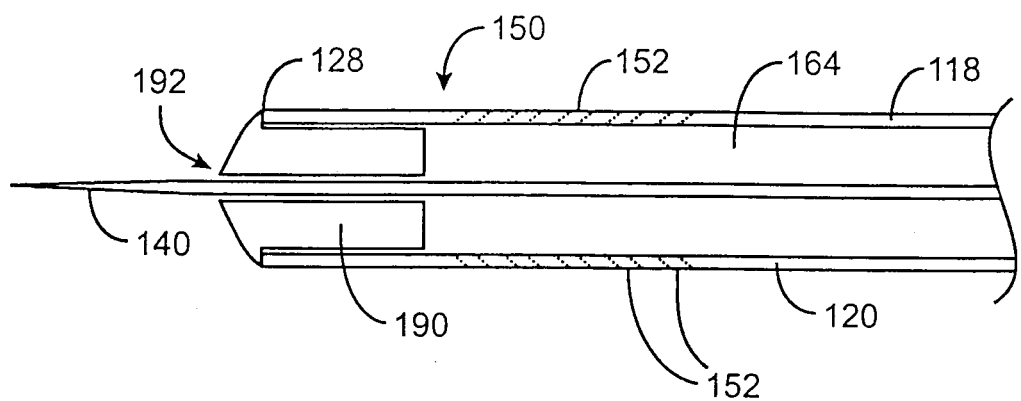
FIG. 12 is a cross section of an alternate construction of the inner catheter tip and rinse head.

FIG. 12 is a cross section of an alternate construction of the inner catheter 120 of the embolization protection system 100. An end cap 190 is fixedly attached within the irrigation lumen 164 at the distal end 128 of the shaft 118 of the inner catheter 120. The end cap 190 has an end hole 192, which has a precision fit with the guidewire 140 that allows the guidewire 140 to slide and rotate with minimal resistance, but that creates a high resistance to fluid flow through the end hole 192 when the guidewire 140 is in place.

This effectively prevents rinsing fluid from flowing out of the end hole 192 and forces it to flow out of the rinse holes or perforations 152 in the rinse head 150.

Figure 13:
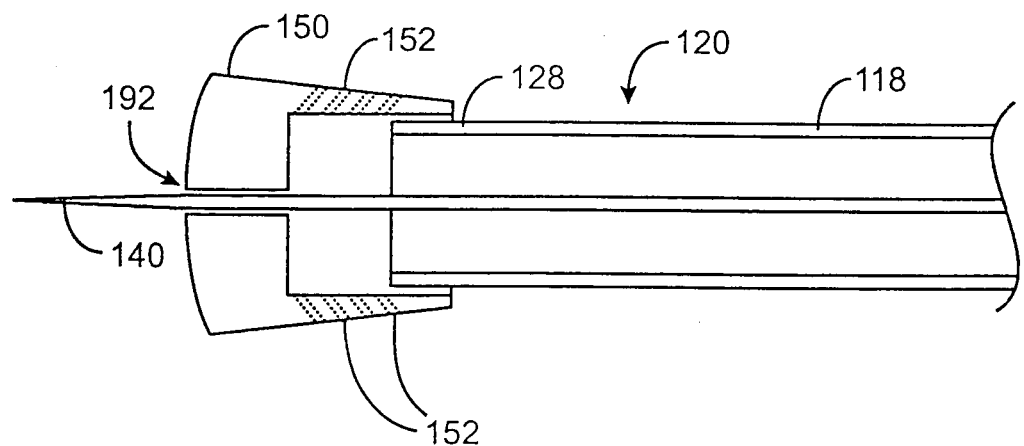
FIG. 13 is a cross section of another alternate construction of the inner catheter tip and rinse head.

FIG. 13 is a cross section of another alternate construction of the inner catheter 120 of the embolization protection system 100. A separately molded, machined and/or laser cut rinse head 150 is fixedly attached to the distal end 128 of the shaft 118 of the inner catheter 120. The rinse head 150 has an end hole 192, which has a precision fit with the guidewire 140 that allows the guidewire 140 to slide and rotate with minimal resistance, but that creates a high resistance to fluid flow through the end hole 192 when the guidewire 140 is in place. This effectively prevents rinsing fluid from flowing out of the end hole 192 and forces it to flow out of the rinse holes or perforations 152 molded, machined or laser cut into the rinse head 150.

Figure 15:
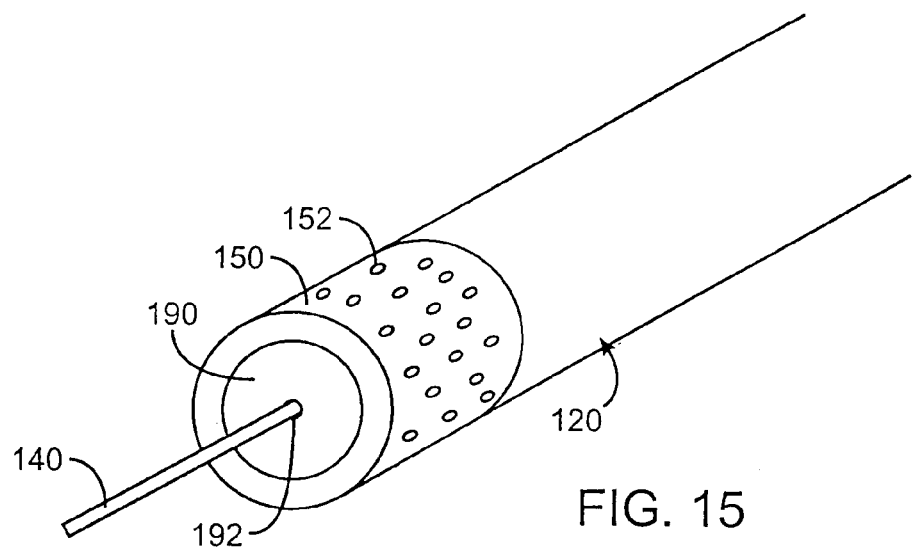
FIG. 15 is a perspective view of the inner catheter tip and rinse head of FIG. 14.
Figure 14:
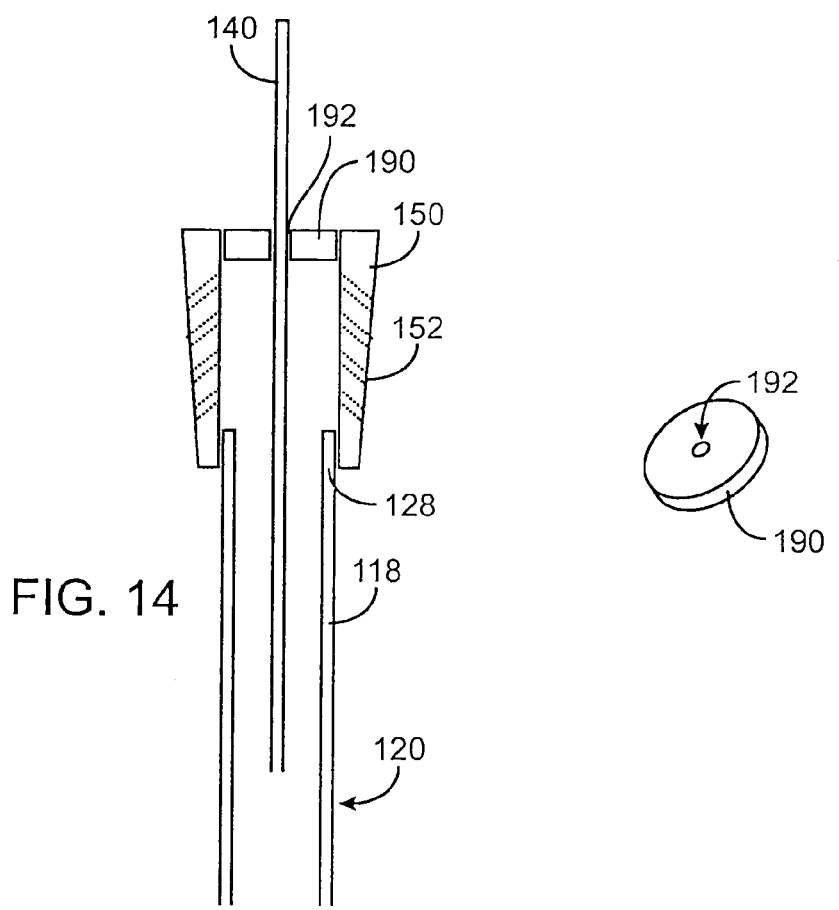
FIG. 14 is a cross section of another alternate construction of the inner catheter tip and rinse head.
Figure 16:
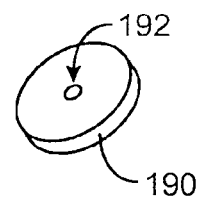
FIG. 16 is a perspective view of the precision fit plug for the inner catheter tip and rinse head of FIG. 14.

FIG. 14 is a cross section of another alternate construction of the inner catheter 120 of the embolization protection system 100. A separately molded, machined and/or laser cut rinse head 150 is fixedly attached to the distal end 128 of the shaft 118 of the inner catheter 120. The rinse head 150 has a tapered tubular configuration. An end cap 190 is fixedly attached within the end of the tubular rinse head 150. The end cap 190 has an end hole 192, which has a precision fit with the guidewire 140 that allows the guidewire 140 to slide and rotate with minimal resistance, but that creates a high resistance to fluid flow through the end hole 192 when the guidewire 140 is in place. This effectively prevents rinsing fluid from flowing out of the end hole 192 and forces it to flow out of the rinse holes or perforations 152 molded, machined or laser cut into the rinse head 150. FIG. 15 is a perspective view of the inner catheter 120 and rinse head 150 of FIG. 14. FIG. 16 is a perspective view of the end cap 190 with the precision fit end hole 192. The end cap 190 may be molded, machined and/or laser cut out of a polymer, such as, but not limited to polyimide, polycarbonate or acrylic. The end hole 192, which is molded, machined or laser cut into the end cap 190, preferably has an inner diameter with approximately 0.0005 to 0.0010 clearance for a sliding fit with the guidewire 140.

The embolization protection system 100 of the present invention can be used in a variety of methods useful in different clinical situations. A method for therapeutic intervention at a lesion, stenosis or other site of interest in a vessel, can be performed as follows:

introducing an occluder to a point in the vessel proximal to the site of interest;
deploying the occluder to occlude the vessel proximal to the site of interest;
aspirating fluid from the vessel proximal to the site of interest;
advancing a rinsing catheter distal to the site of interest;
infusing a rinsing solution through the rinsing catheter to the site of interest;
introducing a treatment device to the site of interest;
deploying the treatment device;
withdrawing the treatment device;
disengaging the infusion;
disengaging the aspiration; and
removing the occluder.

The steps of advancing a rinsing catheter distal to the site of interest and infusing a rinsing solution may be performed prior to and/or after the steps of introducing a treatment device to the site of interest and deploying the treatment device. In one variation of this method, fluid is aspirated at a first, low flow rate from the vessel proximal to the site of interest prior to insertion and deployment of the treatment device and then fluid is aspirated at a second, higher flow rate from the vessel proximal to the site of interest after the treatment device has been withdrawn.

Preferably, the rate of aspiration and rate of infusion are chosen to create a volume exchange of fluid at the site of interest. More preferably, the rate of aspiration and rate of infusion are chosen to create an approximately one-to-one volume exchange of fluid at the site of interest. In some situations it may be advantageous to aspirate more fluid than is infused to insure effective removal of debris and potential emboli or potentially harmful fluids, such as radiopaque dye. Alternatively, a volume exchange of greater or less than one-to-one may be advantageous in some applications. For example, a volume exchange rate of aspiration-to-infusion of approximately one-to-two will provide a downstream flow of fluid, such as oxygenated blood, at a physiologically relevant flow rate at the same time as aspirating debris and potential emboli through the embolic protection system. Volume exchange of fluid at the point of treatment in the vessel is advantageous in that blood is not drawn from the organs downstream of the occluder, such as the brain, which may be vulnerable to ischemic damage or vessel collapse. It also creates a flow containment in the region being treated without the complications and concomitant risks of introducing a second occlusion device distal to the lesion.

The embolization protection system 100 can also be used in a method for diagnosing or treating a selected segment of the vasculature that recovers a substantial proportion of a diagnostic or treatment material that is added to the vessel lumen to aid in diagnosis or treatment. This method may be used for imaging using a diagnostic imaging material, such as a radiopaque dye or an ultrasound contrast agent, and recovering substantially all of the diagnostic imaging material to prevent adverse reactions or systemic effects from the material. Likewise, this method may be used for interventions using a treatment material, such as a thrombolytic agent, plaque decalcification solution or an agent to prevent restenosis, and recovering substantially all of the treatment material to prevent adverse reactions or systemic effects from the material. This method may be performed as follows:

introducing an occluder to a point in the vessel proximal to the selected segment of the vasculature;
    deploying the occluder to occlude the vessel proximal to the selected segment;
    advancing a rinsing catheter distal to the selected segment;
    infusing the diagnostic or treatment material through the rinsing catheter to the selected segment;
    aspirating the diagnostic or treatment material from the vessel proximal to the selected segment;
    disengaging the infusion;
    disengaging the aspiration; and
    removing the occluder.

The apparatus and methods described herein can also be used to enhance various methods of intravascular imaging. Fluid infused into the vessel through the rinse nozzle will displace blood from the region near the distal end of the rinse catheter and towards the opening of the suction lumen. A fluid (e.g. saline solution) that is more transparent than blood at particular wavelengths of light can be used to enhance optical methods for imaging the vessel in the region distal to the distal end of the suction lumen. An imaging catheter or other device can be delivered through the suction lumen of the catheter for optical imaging methods, such as angioscopy or optical coherence tomography. Alternatively, an imaging device, for example a source and/or sensor, can be incorporated into the rinse catheter. Optical coherence tomography is an imaging method that can provide high resolution intravascular imaging of tissue structures. References describing optical coherence tomography include: Brezinski, Circ 93: 1206, 1996. Heart 77:397, 1997; and U.S. Pat. Nos. 6,111,654, 6,134,003 and 6,191,862.

The apparatus and methods described herein can also be used in conjunction with other distal protection devices, such as filters and distal occluders. Okhi et al have shown that 12% of all emboli created during a procedure can occur during the steps associated with crossing the lesion to place the distal protection device. In order to avoid this, the present invention can be used to set up a protective retrograde fluid flow or a static fluid field in the region of the stenosis while placing the distal protection device.

This variation of the method is also particularly beneficial when it is desired to avoid occlusive protection for the full duration of the procedure, for example when the patient would not tolerate full occlusion for long periods because of poor collateral flow. For these patients a nonocclusive distal protection device, such as a filter, may be preferable. However, as mentioned above, placement of the filter distal to the lesion carries with it a significant risk of creating emboli. By combining the benefits of the present invention with a distal filter device, embolic protection can be achieved for the full duration of the procedure while blood flow through the affected artery would only be occluded for a short period in order to place the distal protection device.

Figure 17:
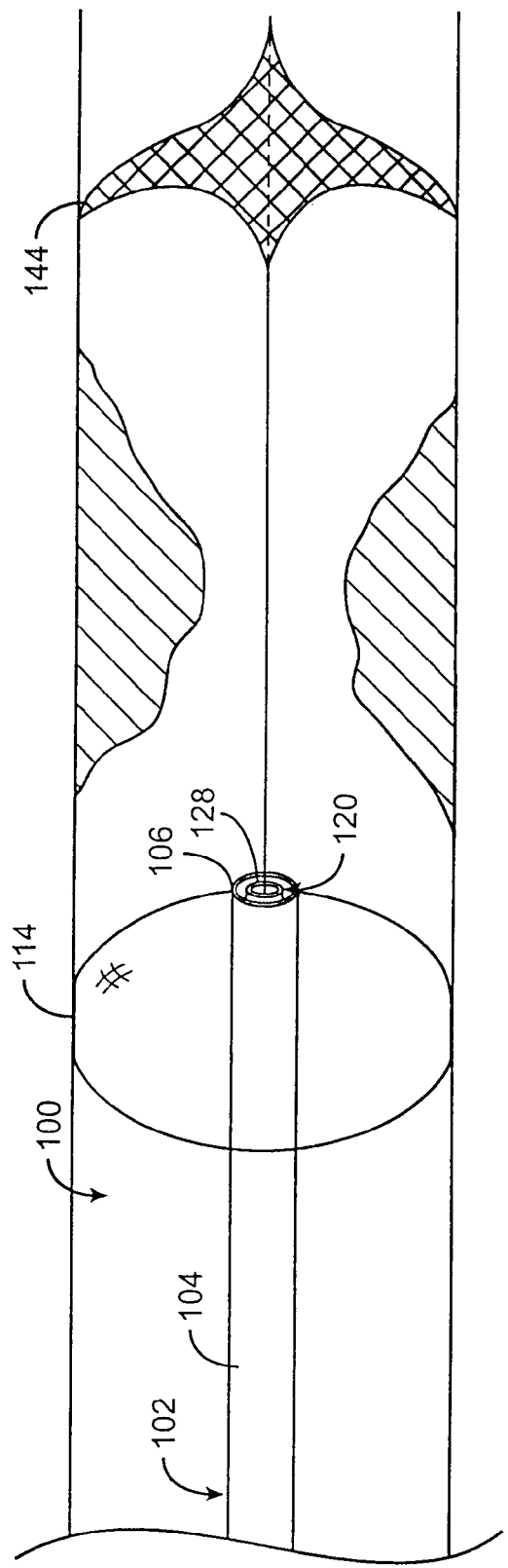
FIG. 17 shows an embolic protection device combined with a distal embolic-protection device in the form of an embolic filter.

FIG. 17 shows an embolic protection device 100 combined with a distal embolic protection device 144 in the form of an embolic filter. Distal embolic protection devices 144 suitable for this application include, but are not limited to, the devices described in U.S. Pat. Nos. 4,794,928, 5,779,716, 6,168,604, 6,203,561, 6,053,932, and 6,129,739. An outer catheter 102 with an occluder 114, as described above, can be used to create a protective retrograde fluid flow or a static fluid field at a lesion or stenosis for safe deployment of an embolic protection device by the following method:

introducing an occluder to a point in the vessel proximal to the site of interest;
    deploying the occluder to occlude the vessel proximal to the site of interest;
    optionally, aspirating fluid from the vessel proximal to the site of interest;
    introducing an embolic protection device distal to the site of interest;
    deploying the embolic protection device;
    undeploying the occluder; and
    disengaging the aspiration.

Once the distal embolic protection is in place, the lesion or stenosis can be treated, as follows:

introducing a treatment device to the site of interest;
    deploying the treatment device; and
    withdrawing the treatment device while the embolic protection device is deployed.

Optionally, a rinsing step may be performed before and/or after deploying the treatment device, as follows:

advancing a rinsing catheter distal to the site of interest prior to introducing the embolic protection device; and
    infusing a rinsing solution through the rinsing catheter to the site of interest while introducing the embolic protection device.

Alternatively, this rinsing step may be performed instead of deploying a treatment device as the only treatment at the site of interest.

Once the treatment and/or rinsing steps are complete, a protective retrograde fluid flow or a static fluid field may be established for safe withdrawal of the embolic protection device, as follows:

deploying the occluder to occlude the vessel proximal to the site of interest;
    optionally, aspirating fluid from the vessel proximal to the site of interest;
    undeploying the embolic protection device;
    withdrawing the embolic protection device from the site of interest;
    undeploying the occluder; and
    disengaging the aspiration.

Optionally, a radiopaque contrast agent or a contrast agent mixed with saline, blood or plasma can be infused to the site of interest through the outer catheter, through the rinsing catheter and/or through a lumen associated with the distal protection device to create a flowing or static field of contrast agent for enhanced imaging of the lesion or stenosis.

In addition, a guidewire or separate guidewires may be used during introduction of the outer catheter, the rinse catheter, the treatment device and/or the distal protection device.

A variation of this method can be of particular benefit when difficulty is encountered in retrieving a distal embolic filter or other distal protection device. Release of captured emboli from a clogged or damaged filter or embolization of parts of the device itself could have dire consequences for a patient, potentially causing damage worse than the condition that was being treated. This method can be used whether or not an occlusion catheter was used for the placement of the embolic filter device. The method for rescuing a troubled filter device is performed as follows:

- introducing a catheter with an occluder over or parallel to the filter device;
- deploying the occluder to occlude the vessel proximal to the filter device to stabilize blood flow;
- advancing a rinsing catheter distal to the lesion site, then rinsing to remove the emboli from the filter while aspirating the emboli out through the occluder catheter; and
- extracting the now empty filter from the treatment site with the occluder in place.

If necessary, the rinsing step may be repeated again after retrieval of the filter. Then, the occluder is undeployed and the catheter is removed. The occluder for this application may be a balloon or a mechanical or self-expanding system, as previously discussed.

Furthermore, the rinsing step may involve thrombolytic agents introduced in the volume exchange model for a localized bathing of the site. Also the treatment may include sonic treatment to help aid in preventing restenosis. The site may also be treated with solutions through the catheter to aid in intimal establishment and to aid in preventing restenosis. A plaque decalcification solution, for example a solution containing HF, may also be introduced through the rinsing catheter 120.

The application of a pre-rinse prior to placement of a stent or other treatment may aid in clearing a wider channel so that the placement of the treatment device is less time consuming. This would be of benefit in cases where the lesion is too tight for the treatment device to cross. A pre-rinse could widen the channel and eliminate the need for predilating the lesion to get the treatment device across.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method to occlude fluid flow in a body vessel and to remove fluid located distal to a site of occlusion, comprising:
   - introducing a catheter into a blood vessel wherein the catheter is comprised of a single occluding member located at the distal end of the catheter, an outer elongated hollow shaft lumen configured for introduction into a blood vessel, and an inner elongated and hollow shaft configured to slide longitudinally within the outer shaft lumen and extendable distal of the occluding member, wherein the inner shaft terminates in a rinse head having one or more rinse holes that traverse a side wall of the rinse head and lacks an expandable occluder;
   - expanding the occluding member to produce a distal occlusion of the body vessel;
   - introducing fluid contents of an inner shaft lumen through the one or more rinse holes in the region distal of the distal occlusion in a flow pattern determined by the arrangement of the one or more rinse holes and directed toward side walls of the body vessel; and
   - removing fluid distal of the distal occlusion through an efflux port in fluid communication with the outer shaft lumen that provides for the removal of fluid and material through an opening distal of the distal occlusion.

2. The method of claim 1 comprising introducing an instrument through a treatment port that provides access to the outer shaft lumen.

3. The method of claim 1, wherein the expandable occluder is inflated through an inflation lumen extending through a separate, hollow elongated shaft that runs parallel to the outer shaft.

4. The method of claim 1, further comprising passing a guidewire through the inner shaft lumen and through an opening in a distal wall of the inner shaft lumen to aid in the delivery of the catheter.

5. The method of claim 1, wherein open-cell foam in fluid communication with an inflation lumen incorporated into the wall of the outer shaft expands the expandable occluder.

6. The method of claim 1, wherein rates of fluid flow through the influx port are manually controlled.

7. The method of claim 1, wherein rates of fluid flow through the influx port is programmably controlled.

8. The method of claim 1, wherein fluid flow within the vessel at or near the treatment site occurs at physiologically relevant flow levels.

9. The method of claim 1, wherein a stent delivery catheter is introduced through the treatment port and the outer shaft lumen.

10. The method of claim 1, wherein an angioplasty catheter introduced through the treatment port and the outer shaft lumen.

11. The method of claim 1, wherein a filter introduced through the treatment port and the outer shaft lumen.

12. A method for occluding flow and providing fluid exchange distal to an expandable occluding member of a catheter, comprising:
   - introducing the catheter comprising an outer elongated and hollow shaft configured for introduction into a blood vessel and an efflux port in fluid communication with a lumen of the outer elongated and hollow shaft;
   - expanding the occluder to create a distal occlusion within the vessel that isolates a region proximal of the occluder from vasculature distal of the occluder;
   - sliding an inner elongated and hollow shaft longitudinally within the outer shaft, wherein the inner and elongated hollow shaft lacks an expandable occluder and wherein the inner shaft terminates in a rinse head having one or more rinse holes that traverse a side wall of the rinse head;
   - introducing fluid contents of an inner shaft lumen to enter the vessel in the region distal of the expandable occluder in a flow pattern determined by the arrangement of the one or more rinse holes and directed toward side walls of the body vessel; and
   - removing fluid and material from the vasculature distal of the distal occlusion through an opening distal of the expandable occluder.

13. The method of claim 12, further comprising introducing an instrument through a treatment port that provides access to the lumen of the outer shaft.

14. The method of claim 12, wherein the at least one opening comprises a multiplicity of openings angled in a proximal direction with respect to a longitudinal axis of the inner shaft.

15. The method of claim 12, wherein the expandable occluder is inflated and an inflation lumen incorporated into a wall of the outer shaft.

16. The method of claim 12, wherein the expandable occluder is inflated through an inflation lumen extending through a separate, hollow elongated shaft that runs longitudinally to the outer shaft.

17. The method of claim 12, further comprising the step of introducing a guidewire that extends through the inner shaft lumen and through an opening in a distal wall of the inner shaft.

18. The method of claim 12, wherein the expandable occluder is self expanding.

19. The method of claim 12, wherein the expandable occluder comprises open-cell foam surrounded by an airtight sheath and the open-cell foam and is expanded by causing the open-cell foam to be exposed to fluid introduced through an inflation lumen incorporated into the wall of the outer shaft.

20. The method of claim 12, further comprising the step of varying rates of fluid flow through the influx port or the outflux port over time in a manually controlled or programmed fashion.

21. The method of claim 12, further comprising introducing a source of radiopaque contrast agent through the inner shaft lumen.

22. The method of claim 12 wherein fluid is delivered only by the inner elongated and hollow shaft.

23. A method to remove emboli distal of a balloon occlusion and in an area of a vessel containing a lesion to be treated comprising:
introducing a catheter having an outer shaft lumen, an occlusive member at the distal end thereof, and an inner shaft lumen that is slidable longitudinally within the outer shaft lumen;
delivering the occlusive member to a position proximal of the treatment site;
expanding the occlusive member to occlude blood flow at a point proximal of the lesion to be treated;
introducing an inner shaft lumen with a fluid ejection nozzle and advancing the nozzle to a point distal of the lesion, the inner shaft lumen lacking an expandable occluder;
introducing the fluid contents of the inner shaft lumen to the point distal of the lesion; and
removing emboli distal of the occlusion balloon by aspirating fluid from the treatment site.

* * * * *